United States Patent [19]
Agwu

[11] Patent Number: 5,350,069
[45] Date of Patent: Sep. 27, 1994

[54] CLEANING AND STORAGE DEVICE

[76] Inventor: David E. Agwu, 1105 Fenimore St., Winston-Salem, N.C. 27103

[21] Appl. No.: 114,683

[22] Filed: Aug. 31, 1993

[51] Int. Cl.⁵ .................... B65D 85/48; A47G 19/08
[52] U.S. Cl. ................................ 206/454; 206/456; 211/41
[58] Field of Search .................. 206/454, 455, 456; 211/41

[56] References Cited

U.S. PATENT DOCUMENTS

| | | | |
|---|---|---|---|
| 2,431,535 | 11/1947 | Bergstrom | 206/454 X |
| 3,826,377 | 7/1974 | Bachmann | 211/41 |
| 4,750,506 | 6/1988 | Qlexa | 211/41 X |

Primary Examiner—William I. Price
Attorney, Agent, or Firm—Olive & Olive

[57] ABSTRACT

A rack device which holds electrophoresis glass plates, clamps, spacers and the like for cleaning and subsequent storage and a method of automated washing and cleaning these components in the rack device.

10 Claims, 3 Drawing Sheets

CLEANING AND STORAGE DEVICE

BACKGROUND OF THE INVENTION

1. Field of the Invention

This invention relates to devices used for automated washing, cleaning and storage of components such as glass plates, clamps, and spacers which are used for vertical gel electrophoresis.

2. Description of the Related Art

Glass plates and other components used in gel electrophoresis must be cleaned between uses. This cleaning requires time-consuming handling of each component, which increases exposure of personnel to toxic chemicals used in the electrophoresis such as acrylamides, as well as resulting in a certain amount of chipping and breakage of the glass plates.

It is therefore an object of this invention to provide a device and method for washing, cleaning and storing gel electrophoresis components, including glass plates, which minimizes handling of the components. It is a further object of this invention to provide a device and method which facilitates the washing process and may be used in the washing process of the glass plates and other components in the same tank or container where the electrophoresis is performed.

Other objects and advantages will be more fully apparent from the following disclosure and appended claims.

SUMMARY OF THE INVENTION

The invention provides a rack device which holds electrophoresis glass plates, clamps, spacers and the like for cleaning and subsequent storage. The invention further provides a method of cleaning these components while in the rack device.

In particular, the invention provides a device for washing and storage of electrophoresis components, comprising a rectangular sheet of material having two parallel first sides and two second sides perpendicular to the first side, with the rectangular sheet having the following cutout portions:

(a) end notches along each first side, with the end notches on one first side being aligned with the end notches on the other first side;
(b) a central opening having two opposite sides;
(c) side notches cut at each opposite side of the central opening, with the side notches on each side being aligned with the side notches on the other side of the central opening, and with the end notches on the first sides;
(d) corner cutout areas adjacent the end notches, wherein the sheet is bent to form a central segment around the central opening which is contiguous with two side segments, each of the side segments being contiguous with a foot segment containing end notches, so that the device may be placed on a surface with the central segment parallel to the surface, the side segments at about a 90° angle to the central segment, and the foot segments at about a 20° angle to the surface on which the device 20 is placed.

Other aspects and features of the invention will be more fully apparent from the following disclosure and appended claims.

DETAILED DESCRIPTION OF THE INVENTION AND PREFERRED EMBODIMENTS THEREOF

The rack device of the invention is preferably made from a flat sheet of a durable, bendable material such as acrylic (methylmethacrylite) plastic, which may be transparent or in a selected color. Acrylic is resilient, light weight, heat resistant, and very durable. It is not adversely affected by the detergent solutions which are recommended for washing the gel electrophoresis components (for example, powder and/or liquid detergent). If the device of the invention is expected to be used in other procedures in the presence of strong acids or alkalis or organic solvents, the material used to manufacture the invention should be appropriately resistant. A sheet of acrylic having a thickness of about 0.25 inch provides sufficient durability and is easily workable to form the device of the invention.

Figure 1:
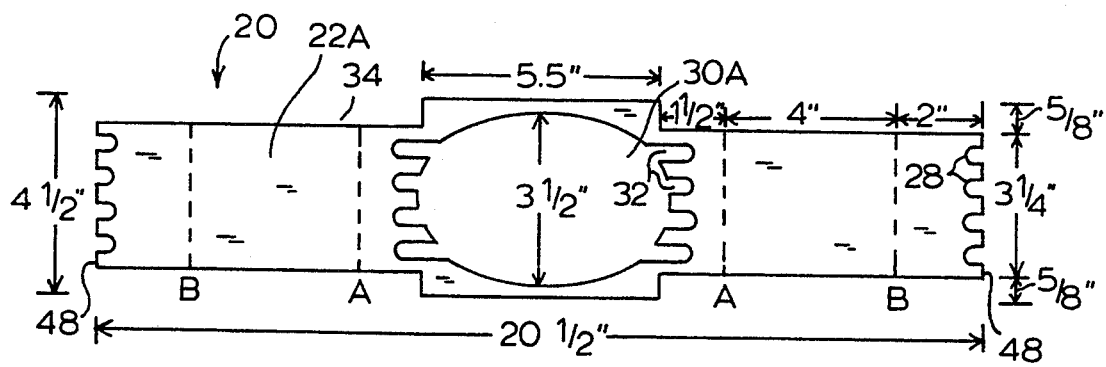
FIG. 1 is a plan view of a rectangular sheet o# material used to make a first embodiment of the rack device of the invention.
Figure 2:
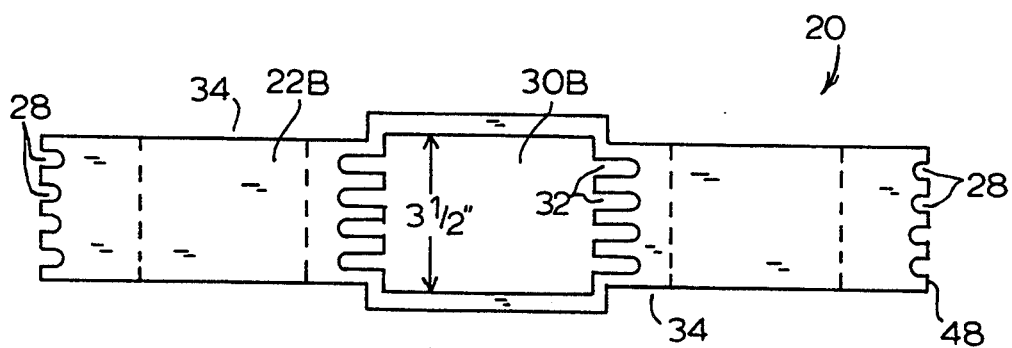
FIG. 2 is a plan view of a rectangular sheet of material used to make a second embodiment of the rack device of the invention.

Referring now to FIGS. 1 and 2, the rack device 20 of the present invention is preferably formed from a rectangular sheet 22A,B of material having two parallel first sides and two second sides perpendicular to said first sides. Preferably the first sides are shorter than the second sides for use of the device with a standard electrophoresis tank 24. For a rack device 20 to be used in a standard electrophoresis tank 24 having interior dimensions of about 5×9.5 inches and for glass plates 26 which are 6.25×7 inches in size, the rectangular sheet 22A,B is preferably about 4.5×20.5 inches. An embodiment of this device which is 6 inches high can be used to clean long plates (7×12⅝ inches) used for long gel electrophoresis in the tank in which such electrophoresis is (was) conducted.

A template having a series of lines indicating where the material is to be cut is placed on the sheet 22A,B. The following cuts are then made. End notches 28, preferably about 0.25 inch in width and about 0.25 inch deep are cut at two opposite sides, preferably shorter sides 48 of the sheet 22A,B so that the end notches 28 at one side 48 of the sheet are aligned with and opposite the end notches 28 at the other opposite side 48 of the sheet. Preferably, there are four notches 28 per side 48 for use with standard size electrophoresis tanks.

A central opening 30A,B which is preferably either oval (FIG. 1) or rectangular (FIG. 2) is cut and side notches 32 are cut at each side of the oval or rectangle. Side notches 32 are aligned with end notches 28. Two notches are "aligned" when both notches are the same distance from, and on the same side of, an imaginary line drawn through the center of the sheet and extending between sides 48 and perpendicular thereto.

A corner strip about ⅜×7 inches is cut from each corner of the rectangular sheet to form corner cutout areas 34.

The cut edges are smoothed and rounded as shown. The sheet 22A,B is then bent along four lines. The bends along the two lines A are made so that there is an angle of about 90° between the material in the central segment 36 surrounding the opening 30A,B and the side segments 38. The material is bent inward at line B so that there is an angle of about 70° between the side segments 38 and the foot segments 40, resulting an angle about 20° between the foot segments and the surface on which the device is placed.

Figure 3:
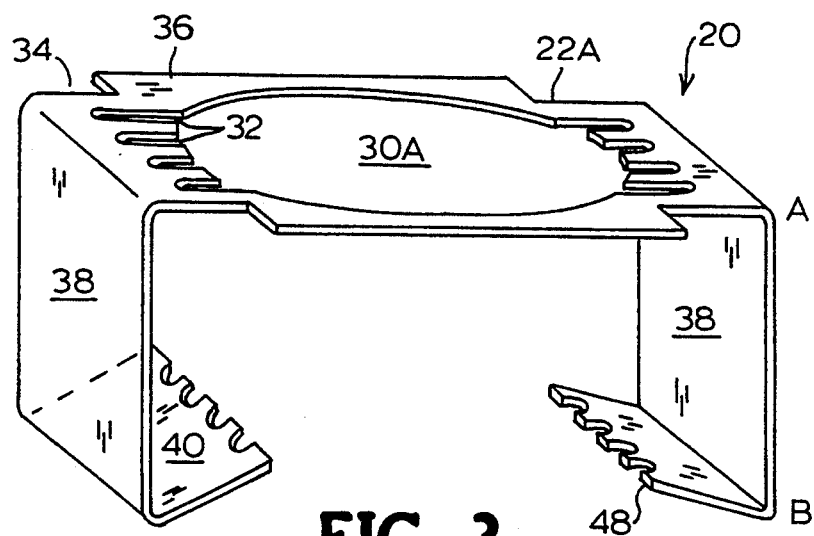
FIG. 3 is a perspective view of the rack device of the first embodiment of the invention which may be formed from the sheet in FIG. 1.
Figure 4:
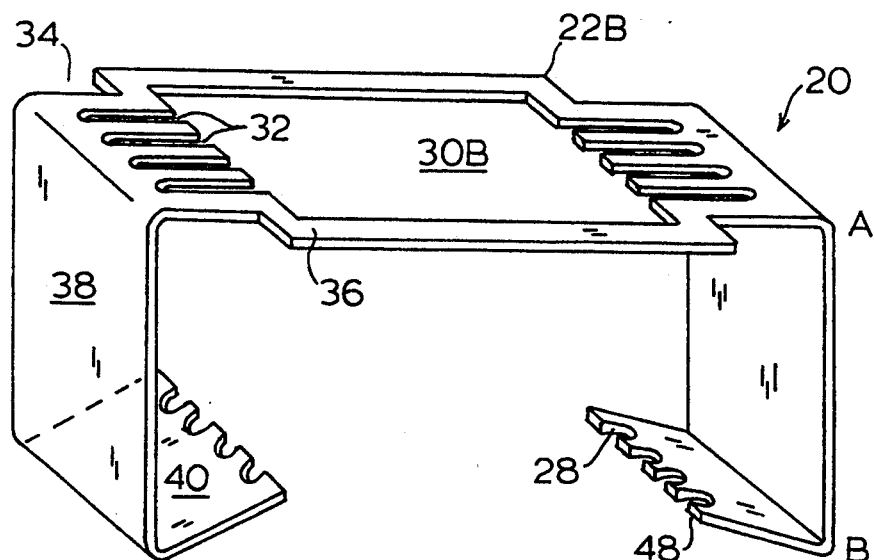
FIG. 4 is a perspective view of the rack device of the second embodiment of the invention which may be formed from the sheet in FIG. 2.
Figure 5:
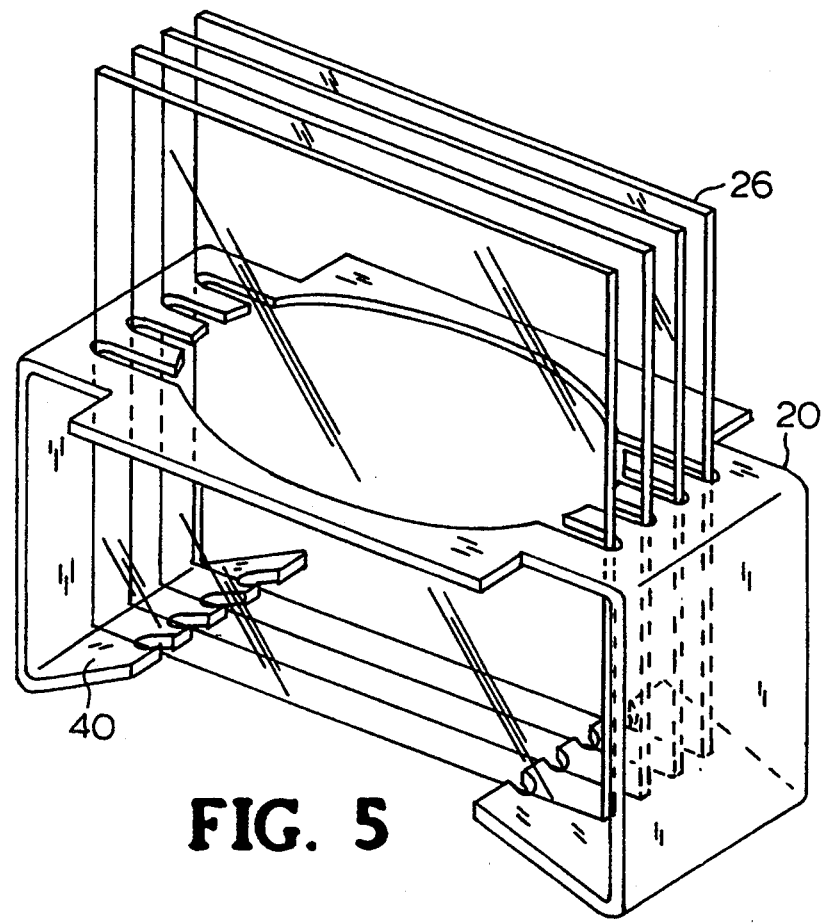
FIG. 5 is a perspective view of a rack device in which glass plates have been placed.
Figure 6:
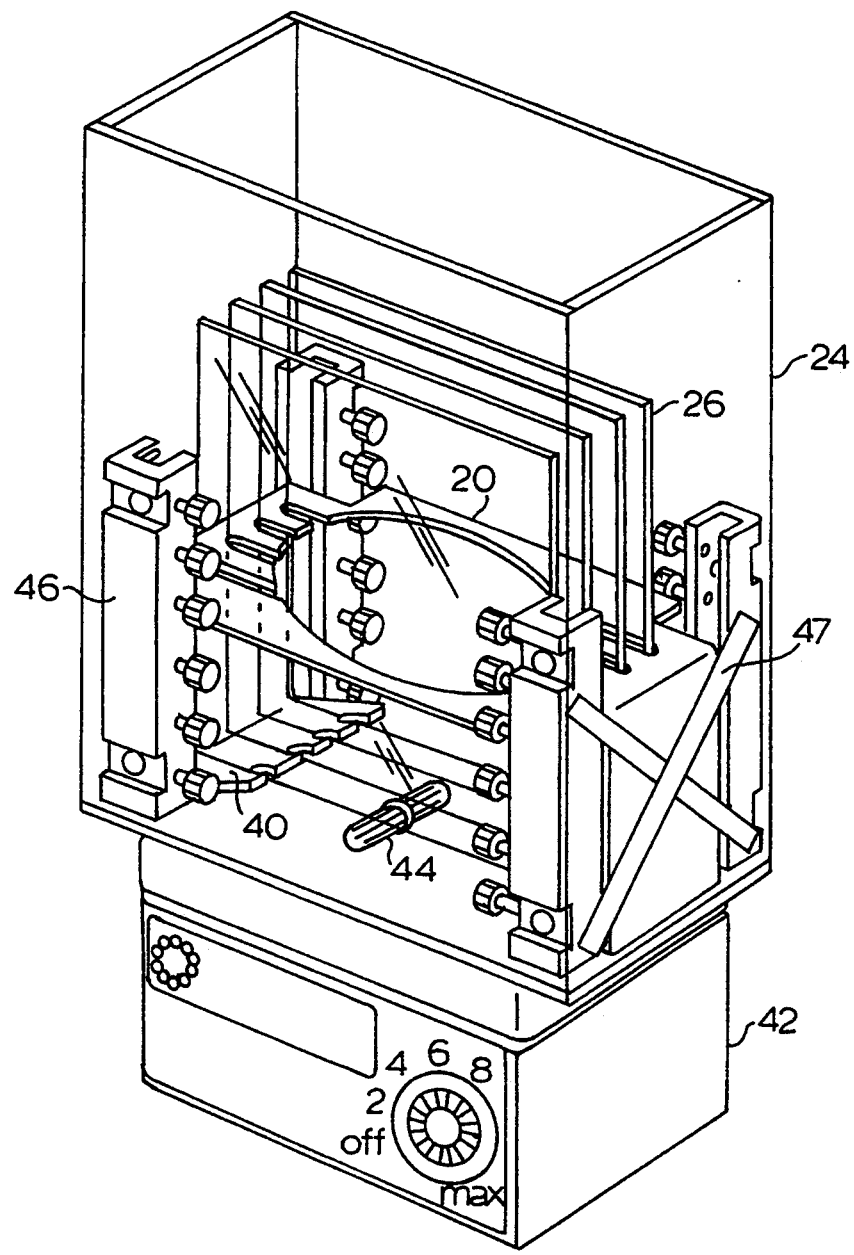
FIG. 6 is a perspective view of an electrophoresis tank and rack device on a magnetic stirrer base.

Glass plates 26 and other components used for gel electrophoresis may be placed in the resultant rack device 20 (FIGS. 3-4) for washing as follows. After electrophoresis, the tank buffer is poured out of the electrophoresis tank 24, and the tank 24 is placed back on an electromagnetic stirrer base 42. The rack device 20 and a magnetic stirrer rod 44 are placed into the tank 24. As the electrophoresis sandwich is dismantled at the end of gel electrophoresis, the components are placed in the rack device 20. The glass plates 26 are placed in the rack device 20 in a tank 24 so that each of the plates 26 is held upright and parallel to the sides of the tank 24 with an and extending between two opposing, aligned side notches 32 on the top of the rack device 20 and within and extending between two opposing, aligned end notches 28 on the two foot segments 40 (FIGS. 5-6). The plates 26 are held above the floor of tank 24 by being held in opposing notches 28 in the angled foot segments 40 as shown in FIGS. 5 and 6. Electrophoresis spacers and clamps 46 may be placed in the spaces formed by the corners of the tank and the corner cutout areas 14. Spacers 47 are placed in the tank as shown in FIG. 6. The components are thus prepared for immediate washing without unnecessary Compartmentalizing the components eliminates contact between them which results in chipping and breakage of the plates when they are soaked together in previous processes.

The rack device 20 of the invention is preferably used for automated washing by adding a reasonable amount of detergent to the tank after addition of the various components as described above, and setting the stirrer to stir vigorously. For best results, particularly if there are problem stains or grease present, the washing is done for up to about two hours. The plates are then removed and scrubbed with wet laboratory towels before replacing them upside down from their former position in the rack device. The washing is continued for another 1-2 hours.

To rinse the electrophoresis components, the tank and its contents are placed under cold running water until bubbles disappear and soapy water is replaced by clean water. Preferably after removing some water for ease of handling, the clamps and spacers are removed to air dry. The rest of the water may then be poured from the tank, using a few folded towels placed over the plates to hold them from falling from the rack device. Each plate may then be rinsed with distilled water, and placed between paper towels to dry. The tank and rack device are individually towel-dried, and rack device may be placed back into the tank.

The plates may be further cleaned with ethanol or isopropanol using a soft tissue. By careful handling of the plates, glass-to-glass contacts and other undesired contact of the plates can be avoided.

After the plates are appropriately cleaned, they are preferably repositioned in the slots as was done for the washing step. The tank may then be covered for short or prolonged storage of the plates.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A device for washing and storage of electrophoresis components, comprising a rectangular sheet of material having two parallel first sides and two second sides perpendicular to said first sides, said rectangular sheet having the following cutout portions:
   (a) end notches along each first side, with the end notches on one first side being aligned with the end notches on the other first side;
   (b) a central opening having two opposite sides;
   (c) side notches cut at each opposite side of the central opening, said side notches on each side being aligned with the side notches on the other side, and with the end notches on the first sides;
   (d) corner cutout areas adjacent said end notches, wherein said sheet is bent to form a central segment around said central opening which is contiguous with two side segments, each of said side segments being contiguous with a foot segment containing end notches, wherein said device may be placed on a surface with said central segment parallel to said surface, said side segments at about a 90° angle to said central segment, said foot segments at an angle to said surface and each of said side notches positioned directly above an end notch, wherein a space is formed between said foot segments, said surface and the lower edge of a glass slide placed in a pair of opposite side notches and in end notches below said pair, which space is of sufficient size to accommodate a magnetic stirrer.

2. A device for washing and storage of electrophoresis components according to claim 1, wherein said material is an acrylic plastic.

3. A device for washing and storage of electrophoresis components according to claim 1, wherein said central opening is oval.

4. A device for washing and storage of electrophoresis components according to claim 1, wherein said central opening is rectangular.

5. A device for washing and storage of electrophoresis components according to claim 1, wherein said foot segments are about at a 20° angle to said surface.

6. A device for washing and storage of electrophoresis components according to claim 1, wherein there are four end notches on each foot segment, and four side notches on each side of said central opening.

7. A device for washing and storage of electrophoresis components according to claim 1, wherein said notches have a depth of about 0.25 inch and a width of about 0.25 inch.

8. A device for washing and storage of electrophoresis components according to claim 1, wherein said sheet of material has dimensions of about 20.5 inch by 4.5 inch.

9. A device for washing and storage of electrophoresis components according to claim 8, wherein said corner cutouts each are about ⅜ inch by 7.5 inches in size.

10. A device for washing and storage of electrophoresis components according to claim 8, wherein said material is bent at about 2 inches and about 6 inches from each first side of said sheet.

* * * * *

UNITED STATES PATENT AND TRADEMARK OFFICE
CERTIFICATE OF CORRECTION

PATENT NO. : 5,350,069
DATED : September 27, 1994
INVENTOR(S) : David E. Agwu

It is certified that error appears in the above-indentified patent and that said Letters Patent is hereby corrected as shown below:

Column 2, line 3, replace "o#" with --of--.

Column 3, line 37, insert --soaking.-- after "unnecessary"

Signed and Sealed this

Seventeenth Day of January, 1995

*Attest:*

BRUCE LEHMAN

*Attesting Officer*     *Commissioner of Patents and Trademarks*